United States Patent [19]

Baur, Jr.

[11] 4,361,552

[45] Nov. 30, 1982

[54] WOUND DRESSING

[75] Inventor: Paul S. Baur, Jr., League City, Tex.

[73] Assignee: Board of Regents, The University of Texas System, Austin, Tex.

[21] Appl. No.: 191,163

[22] Filed: Sep. 26, 1980

[51] Int. Cl.$^3$ .............................................. A61K 35/48
[52] U.S. Cl. ...................................... 424/105; 424/27; 424/95
[58] Field of Search ........................... 424/105, 95, 27

[56] References Cited

U.S. PATENT DOCUMENTS

| | | |
|---|---|---|
| 1,696,958 | 1/1929 | Johnson . |
| 2,039,082 | 4/1936 | Jungmann . |
| 2,143,475 | 1/1939 | Chase . |
| 2,338,416 | 1/1944 | Fales . |
| 2,579,367 | 12/1951 | Curtis et al. . |
| 2,693,438 | 11/1954 | Ward . |
| 2,744,890 | 5/1956 | Wagner et al. . |
| 3,194,732 | 7/1965 | Neuhauser . |
| 3,196,075 | 7/1965 | Neuhauser . |
| 3,272,204 | 9/1966 | Artandi et al. . |
| 3,276,448 | 10/1966 | Kronenthal . |
| 3,304,557 | 2/1967 | Polansky . |
| 3,316,557 | 5/1967 | Liebig . |
| 3,408,659 | 11/1968 | Thiele et al. . |
| 3,438,374 | 4/1969 | Falb et al. . |
| 3,443,261 | 5/1969 | Battista et al. . |
| 3,483,016 | 12/1969 | McCool . |
| 3,491,760 | 1/1970 | Braun et al. . |
| 3,513,485 | 5/1970 | Davila . |
| 3,523,807 | 8/1970 | Gerendas . |
| 3,534,454 | 10/1970 | Okamura . |
| 3,551,290 | 12/1970 | Kawahara et al. . |
| 3,551,560 | 12/1970 | Thiele . |
| 3,563,925 | 2/1971 | Kliment et al. . |
| 3,615,235 | 10/1971 | Schoepfel et al. . |
| 3,655,416 | 4/1972 | Vinson et al. . |
| 3,658,984 | 4/1972 | Kamp . |
| 3,676,298 | 7/1972 | Moczar et al. . |
| 3,688,317 | 9/1972 | Kurtz . |
| 3,733,402 | 5/1973 | Kalopisis et al. . |
| 3,742,955 | 7/1973 | Battista et al. . |
| 3,750,666 | 8/1973 | Graham . |
| 3,767,437 | 10/1973 | Cruz, Jr. . |
| 3,810,473 | 5/1974 | Cruz, Jr. et al. . |
| 3,812,252 | 5/1974 | Silvetti . |
| 3,842,830 | 10/1974 | Hargest . |
| 3,842,831 | 10/1974 | Beisang et al. . |
| 3,849,238 | 11/1974 | Gould et al. . |
| 3,880,158 | 4/1975 | Gurney . |
| 3,908,201 | 9/1975 | Jones et al. . |
| 3,935,308 | 1/1976 | Wise et al. . |
| 3,939,831 | 2/1976 | Cioca et al. . |
| 3,949,742 | 4/1976 | Nowakowski . |
| 3,963,685 | 6/1976 | Abrahams . |
| 3,969,498 | 7/1976 | Catania et al. . |
| 4,014,971 | 3/1977 | Perkins . |
| 4,016,877 | 4/1977 | Cruz et al. . |
| 4,042,978 | 8/1977 | Jones et al. . |
| 4,051,848 | 10/1977 | Levine . |
| 4,060,081 | 11/1977 | Yannas et al. . |
| 4,082,507 | 4/1978 | Sawyer . |
| 4,086,331 | 4/1978 | Neumann . |
| 4,089,333 | 5/1978 | Utsuo et al. . |
| 4,131,650 | 12/1978 | Braumer et al. . |
| 4,161,948 | 7/1979 | Bichon . |
| 4,167,945 | 9/1979 | Gottlieb . |
| 4,193,992 | 3/1980 | Fontaine . |

OTHER PUBLICATIONS

Chem. Abstr., vol. 79, (1973) No. 112521 h.
Bose, B., "Aspects of Treatment, Burn Wound Dressing with Human Amniotic Membrane", Annals of the Royal College of Surgeons of England, 1979, vol. 61, pp. 444–447.
Gruss et al., "Human Amniotic Membrane: Versatile Wound Dressing", CMA Journal, May 20, 1978, vol. 118, pp. 1237 et seq.

*Primary Examiner*—Sam Rosen
*Attorney, Agent, or Firm*—Arnold, White & Durkee

[57] ABSTRACT

A method of treating a wound or burn which comprises covering the surface of the wound or burn with a cross-linked amnion dressing.

21 Claims, No Drawings

WOUND DRESSING

BACKGROUND OF THE INVENTION

1. Field of the Invention

The present invention pertains to methods and materials for treating wounds whether accidentally caused (trauma, burns, etc.) or intentionally created by surgery. In particular, it pertains to the preparation of amnion membranes and methods for treating burns and wounds with this material.

2. Description of the Prior Art

Any injury or surgical procedure that leaves a portion of the body devoid of skin places the organism in dire jeopardy with respect to survival. Essential body fluids escape through large open wounds. Similarly, pathological organisms (fungi, bacteria, microplasms, etc.) easily enter the body through these same sites.

In most cases, wounds are closed by either: physically bringing the margins together vis-a-vis suture material (healing by primary intention) or by allowing the trauma site to heal naturally with new skin growing out and over the wound surface (healing by secondary intention). If the body is able to quickly close the wound opening before pathogens can invade and/or otherwise enter the tissues then the probability of survival is high. However, if wound closure is slow, then the chances of sepsis is high.

If a wound is so large as to prevent the approximation of its margins using sutures, then a dressing has to be used to temporarily seal off the wound from the surrounding environment. The ideal wound dressing should be thin, flexible and inert; provide adequate gas exchange; adhere tightly to the wound surface; prevent microbial invasion; surpress fluid loss; offer a template for new skin growth; should be readily available, easily stored, easily used, relatively cheap, and widely distributed.

The problem of providing a suitable wound dressing has existed since the time when the first open wounds were dressed or covered in order to facilitate healing. The intellectual search for the ideal wound dressing has probably been underway for the past 250 years. Its significance has been recognized for a similarly long period of time because nearly all large (greater than 40% total surface area) burn injuries led to death by bacterial sepsis prior to 1943. The chances for survival were largely improved when the hypochlorite bathing solution was first used (Bunyan-England 1940/1943) the advent of antibiotics and later when the pig skin temporary wound dressing was introduced.

Currently, Open wounds are:
(1) left uncovered and/or untreated;
(2) covered with an anti-bacterial ointment (i.e. silver-sulphadiazine);
(3) temporarily covered with pigskin;
(4) temporarily covered with fresh amnion;
(5) covered by homographic graft from other areas of the body;
(6) covered with heterographic skin (from mother, father, brother, sister, etc.)
(7) covered with a cloth or non-biological membrane or bandage; or
(8) any combination of the above.

None of these are totally acceptable. Pigskin sloughs off after twenty to twenty-five days due to an antigen/antibody reaction. Fresh amnion can be enzymatically digested by the host in three to four days if the area covered is moist. Amnion may also evoke an antigen-antibody reaction and there is also a risk of transferring pathogens from donor to recipient. Homographic skin grafts cover one area while opening up another at the donor site. Heterographic skin is usually rejected by the patient in six to twenth-five days (another antigen/antibody reaction).

Because human amnion, being a continuation of the fetal integument, has many of the natural and physical qualities of skin and is relatively cost effective, it has become more popular as a temporary dressing than porcine xenografts in some burn treatment institutions. The successful use of fresh and/or frozen amnion as a biological dressing (i.e. on burn wounds), depends in part on its structure an integrity as a microbial barrier and on the sterility of the membrane, as well as the condition and nature of the wound to which it is applied.

Although amnion is a popular temporary dressing, in many ways it is even more temporary than pigskin or heterographic skin. Electronmicroscopy reveals the near total degradation of amnion by the host as early as three days post application if the covered site remains moist. The degradation appears to be due to digestion by enzymes in the wound exudate observable as early as twenty-four hours after application. Ultra-structural features of the amnion dermis, epidermis and basal lamina are completely lost after forty-eight hours on the patient. After seventy-two hours, the membrane components are difficult if not impossible to discern. Thus, the barrier qualities of the sterile fresh amnion may be lost long before the patient's need for barrier protection has ended. It is now recommended that, when used on severe wounds, the amnion be replaced at approximately three day intervals. In addition, electron microscopy discloses that some of the collagen filaments in the amnion dermis are partially unraveled during sterilization procedures (which usually empolys a sodium hypochlorite solution) required to render the amnion aseptic which further compromises the barrier quality of the membrane even prior to its application to the wound.

SUMMARY OF THE INVENTION

In the present invention, a wound dressing is provided from amnion, treated in such a way that it becomes a substantially more permanent dressing until the wound is healed. Fresh amnion from any animal source is fixed or stabilized by glutaraldehyde solutions or any other fixing or tanning solution so that the proteins thereof are cross-linked. Due to such change in the physical nature of the proteins comprising the structure of the amnion, the host's enzymes can no longer digest or break it down. Its physical properties (strength, flexibility, etc.) are also improved. Other objects and advantages of the invention will be understood from reading the specification which follows.

DESCRIPTION OF THE INVENTION

To prepare a wound dressing according to the present invention, amnion is collected from any suitable animal species (human, cattle, pigs, etc.) from term or near term fetuses at the time of delivery or slaughter. The amnion is excised away from the umbilical cord, freed of chorion material by gentle scraping and rinsed with sterile saline. Alternately the chorion could be removed by gentle scraping after fixation to be described hereafter. All processing should be carried out under sterile or semisterile conditions.

The amnion is then fixed in a suitable fixing solution for a period of time from a few hours to a few days, depending upon the type of fixing solution and the concentration used. Typical fixing agents can be selected from the group consisting of glyoxal, glutaraldehyde, hydroxyadipaldehyde, pyruvic aldehyde, crotonaldehyde, acetaldehyde, acrolein, methacrolein, formaldehyde, malonaldehyde, succinaldehyde, and chromic acid. Combinations of fixatives may be used. For instance, 0.6%, 3% or 6% glutaraldehyde solutions have been found to sufficiently fix the tissue in twenty-four to forty-eight hours. However, it appears that a range of from 0.001% to 25% concentrations of glutaraldehyde are workable, the stronger solutions requiring a fixation time of from two or three hours and the weaker solutions requiring three or four weeks. Excessive fixation does not appear to affect the quality of the membrane.

The minimum ratio of fixing solution volume to amnion volume should also be considered. In a 0.6% glutaraldehyde solution, a ratio of around fifty is required. Of course, the ratio is smaller for greater solution concentrations (25% glutaraldehyde a ratio of 1–5) and larger for smaller concentration solutions (0.001% a ratio of 1000).

The fixing solution should be buffered with a buffer that produces a stabilized membrane that is compatible with life, i.e. phosphate, bicarbonate, barbital, etc. The buffer should be in the range of 0.001 to 0.2 m (mols), and have a pH of 6.5 to 8.4. The osmolarity of the solution should ideally be around isotonic conditions (300 mOs) or perhaps even slightly hypertonic (600 mOs). However, a range of 50 to 2,000 mOs is acceptable depending upon solution concentrations. The osmolarity of the fixative solution is usually determined by the fixative and buffer concentrations. Inert materials (salts, sugars, etc.) may also be added to the solution in order to increase its osmolarity.

After fixing, the amnion is prepared for storage. It may be stored in a liquid phase, air-dried or lyophilized (freeze dried). If stored in solution, the amnion may be shaped into utilizable pieces, rolled in Nylon mesh gauze and transferred to a maintenance solution of the same fixing materials, i.e. 0.6% to 3.0% glutaraldehyde solution with buffer or any other antiseptic solution, saline or even distilled water. The material is then placed in sterile containers and stored preferably at 0° to 4° C., but up to 25° C.

Anatomically, the stabilized amnion material is found to exist in three parts, the epidermal layer, the basement membrane, and an underlying connective tissue layer similar to the dermis of skin. The epidermis is comprised of a single layer of cuboidal cells closely attached to one another. After fixation (chemical stabilization) the cells are no longer viable. The epidermis rests on a basement membrane layer or basal lamina which is comprised of a fibrillar proteinacious layer approximately three to five microns thick. This membrane is for the most part intact without obvious voids which would permit pathogen invasion. The underlying connective tissue (comprised of a compact layer, a fibroblast layer, and a spongy layer) but for simplicity's sake henceforth referred to as the amnion dermis is comprised of a layer of tightly packed collagen filaments fused into a solid mass of fibers. Under this solid fiber mat are to be found a looser arrangement of collagen fibers and filaments. All of the proteins in the amnion are cross-linked by the stabilization process. Occasionally fibrocytic cells can be found in this layer. Hence, the cells, the interstitial materials (collagen, ground substances, etc.) and the occasional vascular components (small capillary remnants in the deep dermis) are chemically fixed or precipitated by the stabilizing or fixing solution or process.

The stabilized amnion material, after fixation, shows a increase in tensile strength while not being appreciably changed with respect to structural organization, thickness, coloration, etc. No dermal appendages (glands, hair follicles, etc.) or holes are normally found in the amnion. It is a homogeneous biological membrane.

After preparation, the amnion prosthesis can be brought from the storage fluid and rinsed several times using sterile saline. Minimum rinsing changes, times and volumes will depend on the amount of amnion material used and the type of storage solution employed. However, the rinses are intended to reduce the free glutaraldehyde (or other fixative) concentration in the final solution to an acceptable human allowance. The rinses should be carried out under sterile conditions.

If the stabilized amnion is to be air-dried, it would be rinsed after fixation in water and dehydrated through a series of alcohol ending in a 100% ethyl alcohol bath or any other acceptable organic solvent such as freon, acetone, etc. Then the amnion membrane would be air-dried, packaged and sterilized. It may be sterilized in an appropriate gas, i.e. ethylene dioxide or formaldehyde gas, or with high levels or gamma radiation (i.e. 2,000,000 rads).

The fixed amnion could also be dried by lyophilization procedures which are ideal for biological wound dressings. In such procedures, the fixed amnion would be rinsed with saline and then water followed by cryogenic freezing, i.e. with liquid nitrogen at $-185°$ C. The frozen material is then subjected to high vacuum causing the water to sublimate. Sterilization would be the same as in air-drying.

To use on the wound, the hydrated amnion prosthesis is unrolled, removed from the Nylon mesh netting, if there is such, placed over the wound surface (the amnion dermis placed downward) and held in place by bandaging, sutures or allowed to attach by wound serum dessication (coagulation). When dried amnion is used, it quickly imbibes the plasma from the wound surface, evokes platelet activity and becomes tightly attached.

The prosthesis can be used on any open wound that has been properly cleaned and debrided. The wounds can be full-thickness skin loss caused by: excisional trauma, abrasion, thermal or chemical trauma or surgical excision. Similarly, the material can be used on wounds that are intended to heal by means of secondary intention (wounds produced by pilonidal cyst excision, fistulectomies, etc.). How the amnion is first physically attached (i.e. adherence, sutures, etc.) to the wound is an unimportant aspect, but efforts should be made to allow the prosthesis to stabilize on the wound surface for the first few hours to allow its complete attachment. In most cases, the amnion quickly and tenaciously attaches to the wound surface; especially when dried or lyophilized membrane is used.

Underlying wounds are then allowed to heal under the amnion covering. Surveillance should be maintained for any obvious pockets of purulent material that may form under the amnion although this is rare. As the membrane is extremely thin and nearly transparent, surveillance is easy. Should localized areas of contamination form, then the amnion can easily be excised away from these small areas, the wound cleansed in that area and a smaller stabilized amnion patch used.

The amnion appears to detach from the wound after epithelization and keratinization has taken place. In very large surface wounds, mesh homographic skin tissue should be situated between the wound surface and the amnion covering to provide a source for epidermal cells and to accelerate the process of total epithelization.

The fixed amnion dressing can be used for long periods without need of replacement or fear of eliciting a host/graft response. This is due to the resultant inertness of the material after fixation. The dermis of the stabilized amnion also provides a pattern for the synthesis, deposition and orientation of the host's new dermis (collagen fibers). The amnion provides a suitable wound barrier which cannot be compromised by enzymatic degradation either mediated by the host or by invasive microorganisms. The amnion membrane is devoid of hair follicles, glands, etc. whose structural configuration would otherwise provide crypts, folds and/or passages through which microbial access would be provided to the wound environment. It provides a suitable mechanical and water barrier to the wound tissue and as such provides structural integrity and prevents excessive fluid loss. The stabilized amnion skin prosthesis (in that it is fetal skin) is the perfect wound dressing and/or temporary skin. Additionally, fixation reduces the risk of pathogen transfer from donor to recipient to an extremely low level or even zero. Viruses, bacteria and fungi that normally may reside in an amnion are all killed by the processing procedure.

The fixed amnion prosthesis used as a wound dressing is a substantial advancement in the wound healing art in that the material remains in place, intact and uncompromisable until the recipient host tissue (wound) no longer needs it and it simply falls off. It does not and cannot evoke a host/graft response (antigen/antibody reaction) and therefore does not seem to influence the recipient's immune system. It appears to be biologically inert and as such is safer than synthetic membranes that might contain unsafe organic compounds. The physical nature of the stabilized amnion material encourages would repair by offering a template upon which new collagen fibers can be laid down. The strength of the stabilized amnion material also contributes to the integrity of underlying delicate wound healing tissues and as such appears to suppress wound contraction.

The epidermal cells of the host tissue grow between the stabilized amnion material and the wound surface. Upon differentiation of the newly formed epidermal layer and the keratinization of this layer of cells, the stabilized amnion material is dessicated and as such is quietly released and falls off. No invasive procedures are required after the stabilized amnion material is in place. Pain in the wound is immediately attenuated and/or alleviated after the membrane is applied.

Unexpected properties suggest that stabilized amnion material may be used in other areas of biological endeavor. Items such as artificial tempanic membranes, tendons, ligaments, etc. may be produced from this inert material. Unexpected results include leukocytic aggregation at the surface of the stabilized amnion material after placement on the wound. These cells appear to be involved in a benign foreign body reaction. A layer of leukocytes provides an additional barrier to pathogen invasion, as well as generating an adherence of viable cells to the inert stabilized amnion material. This reaction also appears to keep the material hydrated through the course of repair with dehiscence occurring in the stabilized amnion material in those areas after the wound has healed (epidermis forms, differentiates, and keratinizes).

Experiments suggest that the stabilized amnion material is antigenically inert. When placed subcutaneously in a recipient, it evokes only a foreign body reaction (becomes encapsulated) but does not produce a typical immulogical response. Ultrastructurally, the stabilized amnion remains intact when placed on the surface of experimental wounds, burns and in the subcutaneous capsules for long periods of time. Healing tissue under the amnion cover appears to be at least equal to but more commonly better than that observed in untreated wounds. For instance the dermis is thicker, more ordered and observed to be structurally more normal and the size of the wound is not diminished by wound contraction.

Millions of individuals are burned and severely wounded annually throughout the world. Burns and wounds requiring a wound dressing are all subjects for the stabilized amnio material prosthesis of the present invention. The stabilized amnion material prosthesis would stay in place until reepithelization, grafting, etc. had taken place, not being compromised by the host or microbes and maintaining its integrity until the wound has healed. The stabilized amnion material is tough, flexible and durable.

The fresh human amnion and pigskin currently used as temporary wound dressings are expensive to obtain and prepare, difficult to store and are of limited availability. In comparison, the stabilized amnion material can be produced easily and cheaply, stored in small packages (in dry or hyrated states) under normal refrigeration (materials stored in fixative solutions) or even unrefrigerated for ready distribution and employment not only in burn wards, hospitals and medical centers, but by clinicians anywhere at any time. In addition to being used as a wound dressing, it can be used for artificial fascia, artificial tendons, supportive ligaments, tempanic membranes or anywhere an artificial membrane might provide a support, partition, isolation or structure for the recipient.

While a few variations of the invention have been described herein, many others may be made without departing from the spirit of the invention. Accordingly, it is intended that the scope of the invention be limited only by the claims which follow.

I claim:

1. A method of treating a wound or burn comprising the covering of said wound or burn with a dressing formed of amnion in which the proteins have been fixed by cross-linking.

2. The method of claim 1 in which said amnion dressing is formed by stabilizing the proteins of the amnion with a solution containing a chemical cross-linking agent.

3. The method of claim 2 in which said chemical cross-linking agent is selected from one or more of the group consisting of glyoxal, glutaraldehye, hydroxyadipaldehyde, pyruvic aldehyde, crotonaldehyde, acetaldehyde, acrolein, methacrolein, formaldehyde, malonaldehyde, succinaldehyde and chromic acid.

4. The method of claim 2 in which the concentration of said chemical cross-linking agent in said solution is from 0.001% to 25%.

5. The method of claim 4 in which said amnion is fixed in said solution for a period of from two hours to four weeks.

6. The method of claim 4 in which said solution is buffered with an osmolarity buffer so that said solution has an osmolarity of from 50 mOs to 2,000 mOs.

7. The method of claim 2 in which said cross-linked amnion is prepared for storage by storing in an antiseptic, saline or distilled water maintenance solution and maintained at a temperature of from 0° C. to 25° C.

8. The method of claim 7 in which said cross-linked amnion prepared for use by rinsing until the concentration of free chemical cross-linking agent from said maintenance solution is reduced to acceptable human tolerance in said amnion.

9. The method of claim 2 in which said cross-linked amnion is prepared for storage by rinsing until the concentration of said chemical cross-linking agent in said solution is reduced to acceptable human tolerance, air-drying and sterilizing.

10. The method of claim 9 in which said cross-linked amnion is dehydrated in an acceptable organic solvent prior to said air-drying thereof.

11. The method of claim 2 in which said cross-linked amnion is prepared for storage by rinsing until the concentration of said chemical cross-linking agent in said solution is reduced to acceptable human tolerance, subjecting said rinsed cross-linked amnion to lyophilization, and sterilizing.

12. A dressing for wounds, burns and surgically affected body members comprising amnion, the proteins of which have been cross-linked by fixing in a solution of a chemical cross-linking agent capable of cross-linking the proteins of said amnion.

13. A dressing as set forth in claim 12 in which said solution includes a chemical cross-linking agent selected from one or more of the group consisting of glyoxal, glutaraldehyde, hydroxyadipaldehyde, pyruvic aldehyde, crotonaldehyde, acetaldehyde, acrolein, methacrolein, formaldehyde, malonaldehyde, succinaldehyde and chromic acid.

14. A dressing as set forth in claim 12 in which the concentration of said chemical cross-linking agent in said solution is from 0.001% to 25%.

15. A dressing as set forth in claim 14 in which said amnion is fixed to said solution for a period of two hours to four weeks.

16. A dressing as set forth in claim 14 in which said solution is buffered with an osmolarity buffer so that said solution has an osmolarity of from 50 mOs to 2,000 mOs.

17. A dressing as set forth in claim 13 in which said cross-linking amnion is prepared for storage by storing in an antiseptic, saline or distilled water maintenance solution and maintained at a temperature of 0° C. to 25° C.

18. A dressing as set forth in claim 17 in which said cross-linked amnion is prepared for use by rinsing until the concentration of free chemical cross-linking agent from said maintenance solution is reduced to acceptable human tolerance in said amnion.

19. A dressing as set forth in claim 12 in which said cross-linked amnion is prepared for storage by rinsing until the concentration of said chemical cross-linking agent in said solution is reduced to acceptable human tolerance, air-drying and sterilizing.

20. A dressing as set forth in claim 19 in which said cross-linked amnion is dehydrated in an acceptable organic solvent prior to said air-drying thereof.

21. A dressing as set forth in claim 12 in which said cross-linked amnion is prepared for storage by rinsing until the concentration of said chemical cross-linking agent in said solution is reduced to acceptable human tolerance, subjecting said rinsed cross-linked amnion to lyophilization, and sterilizing.

* * * * *